US008551472B2

(12) United States Patent
Senju

(10) Patent No.: US 8,551,472 B2
(45) Date of Patent: Oct. 8, 2013

(54) METHOD OF MAKING MACROPHAGE EXPRESSING AN ANTIBODY DIRECTED AGAINST β-AMYLOID

(75) Inventor: Satoru Senju, Kumamoto (JP)

(73) Assignee: National University Corporation Kumamoto University, Kumamoto (JP)

( * ) Notice: Subject to any disclaimer, the term of this patent is extended or adjusted under 35 U.S.C. 154(b) by 0 days.

(21) Appl. No.: 13/265,626

(22) PCT Filed: Apr. 16, 2010

(86) PCT No.: PCT/JP2010/056862
§ 371 (c)(1),
(2), (4) Date: Jan. 12, 2012

(87) PCT Pub. No.: WO2010/122961
PCT Pub. Date: Oct. 28, 2010

(65) Prior Publication Data
US 2012/0122214 A1    May 17, 2012

(30) Foreign Application Priority Data

Apr. 24, 2009 (JP) ................................. 2009-105894
Dec. 22, 2009 (JP) ................................. 2009-290152

(51) Int. Cl.
*A61K 48/00* (2006.01)
*C12N 5/00* (2006.01)
*C12N 15/00* (2006.01)

(52) U.S. Cl.
USPC ........................................ 424/93.21; 435/325

(58) Field of Classification Search
USPC ................................................ 435/325, 455
See application file for complete search history.

(56) References Cited

U.S. PATENT DOCUMENTS

| 2008/0014178 A1 | 1/2008 | Koistinaho et al. |
| 2010/0081199 A1 | 4/2010 | Slukvin et al. |
| 2011/0104102 A1 | 5/2011 | Koistinaho et al. |

FOREIGN PATENT DOCUMENTS

| WO | WO 2004080419 A2 * | 9/2004 |
| WO | 2006/005802 | 1/2006 |
| WO | 2006/022330 | 3/2006 |
| WO | 2007/069666 | 6/2007 |

OTHER PUBLICATIONS

Senju et al. cited on IDS Jan. 12, 2010 #3.*
Moore (2002, DNA and Cell Biol., vol. 21(5/6), pp. 443-451).*
Thomson (1995, PNAS, vol. 92, pp. 7844-7848).*
NIH (Stem Cells: Scientific Progress and Future Research Directions, Department of Health and Human Services, Chapter 1, Jun. 2001).*
NIH (Stem Cells: Scientific Progress and Future Research Directions, Department of Health and Human Services, Chapter 3, Jun. 2001).*
Takahashi (Cell, 2006, vol. 126:663-676).*
Yu (Science, Nov. 20, 2007, vol. 318, p. 1917-1920).*

(Continued)

*Primary Examiner* — Michael C. Wilson
(74) *Attorney, Agent, or Firm* — Greenblum & Bernstein, P.L.C.

(57) ABSTRACT

It is an object of the present invention to provide a method for producing a cell medicine that is effective for diseases while causing a low risk to these diseases. The present invention provides a method for producing a phagocyte that expresses a foreign protein, which comprises: a step of introducing a protein expression vector into an induced pluripotent stem cell; and a step of inducing the induced pluripotent stem cell, into which the protein expression vector has been introduced, to differentiate into a phagocyte.

5 Claims, 12 Drawing Sheets

(56) References Cited

OTHER PUBLICATIONS

Blelloch (Cell Stem Cell, Sep. 13, 2007, vol. 1, p. 245-247).*
Nakagawa (Nat Biotechnol, Jan. 2008, vol. 26: 101-106).*
Senju (Stem Cells, Feb. 2009, vol. 27, pp. 1021-1031).*
Burke (J. Leukoc. Biol., 2002, vol. 72, p. 417-428).*
Burke (Expert Opin. Biol. Ther., 2003, vol. 3, p. 919-924).*
Senju ("Development of medical technology using iPS cell-derived dendritic cells and macrophages," Regenerative Medicine (Saisei Iryo), 2008, vol. 7, p. 259-261).*
Senju ("Immunotherapy using ES cells and iPS cells," Journal of Clinical and Experimental Medicine (Igaku no ayumi), 2008, vol. 227, p. 413-418).*
Bolmont et al., "Dynamics of the Microglial/Amyloid Interaction Indicate a Role in Plaque Maintenance" *The Journal of Neuroscience*, vol. 28, No. 16, pp. 4283-4292, XP55035877 (2008).
Choi et al., "Hematopoietic and Endothelial Differentiation of Human Induced Pluripotent Stem Cells" *Stem Cells*, vol. 27, No. 3, pp. 559-567, XP55035783 (published online Jan. 8, 2009).
Lu et al., "Avian-Induced Pluripotent Stem Cells Derived Using Human Reprogramming Factors" *Stem Cells and Development*, vol. 21, No. 3, pp. 394-403, XP55035958 (published online Oct. 4, 2011).
Senju et al., "Generation of dendritic cells and macrophages from human induced pluripotent stem cells aiming at cell therapy" *Gene Therapy*, vol. 18, No. 9, pp. 874-883, XP55027827 (published online Mar. 24, 2011).
Extended European Search Report for European Patent App. No. 10767018.4, dated Aug. 28, 2012.
"iPS" 2008, pp. 259-261, vol. 7.
"ES, iPS", 2008, pp. 413-418, vol. 227.
Senju et al., "Characterization of dendritic cells and macrophages generated by directed differentiation of mouse induced pluripotent stem cells", Stem Cells, Feb. 13, 2009, pp. 1021-1031, vol. 27.
Burke et al., "Macrophages in gene therapy: cellular delivery vehicles and in vivo targets", J. Leukoc. Biol., 2002, pp. 417-428, vol. 72.
Burke, "Macrophages as novel celluar vehicles for gene therapy", Expert Opin. Biol. Ther., 2003, pp. 919-924, vol. 3.
Griffiths et al., "The macrophage—a novel system to deliver gene therapy to pathological hypoxia.", Gene Ther., 2000, pp. 255-262, vol. 7.
Paul et al., "Redirected cellular cytotoxicity by infection of effector cells with a recombinant vaccinia virus encoding a tumor-specific monoclonal antibody.", Cancer Gene Ther., 2000, pp. 615-623, vol. 7.
Paul et al., "Targeted macrophage cytotoxicity using a nonreplacative live vector expressing a tumor-specific single-chain variable region fragment.", Human Gene Ther., 2000, pp. 1417-1428, vol. 11.
Fukushima et al., "Idenshi Kaihen iPS Saibo Yurai Kijo Saibo Oyobi Macrophage ni yoru Melanoma no Men'eki Ryoho", Nippon Hifuka Gakkaishi, Mar. 15, 2010, pp. 775, vol. 120.
Choi et al., "Generation of mature human myelomonocytic cells through expansion and differentiation of pluripotent stem cell-derived lin-CD34+CD43+CD45+ progenitors", J. Clin. Invest., Aug. 10, 2009, pp. 2818-2829, vol. 119.
International Preliminary Report on Patentability for International Application No. PCT/JP2010/056862, mail date is Nov. 17, 2011 (Japanese and English versions).
Search report from International Application No. PCT/JP2010/056862, mail date is May 25, 2010.
Senju, "Development of medical technology using iPS cell-derived dendritic cells and macrophages," Regenerative Medicine (Saisei Iryo), 2008, vol. 7, pp. 259-261.
Senju, "Immunotherapy using ES cells and iPS cells," Journal of Clinical and Experimental Medicine (Igaku no ayumi), 2008, vol. 227, pp. 413-418.

* cited by examiner

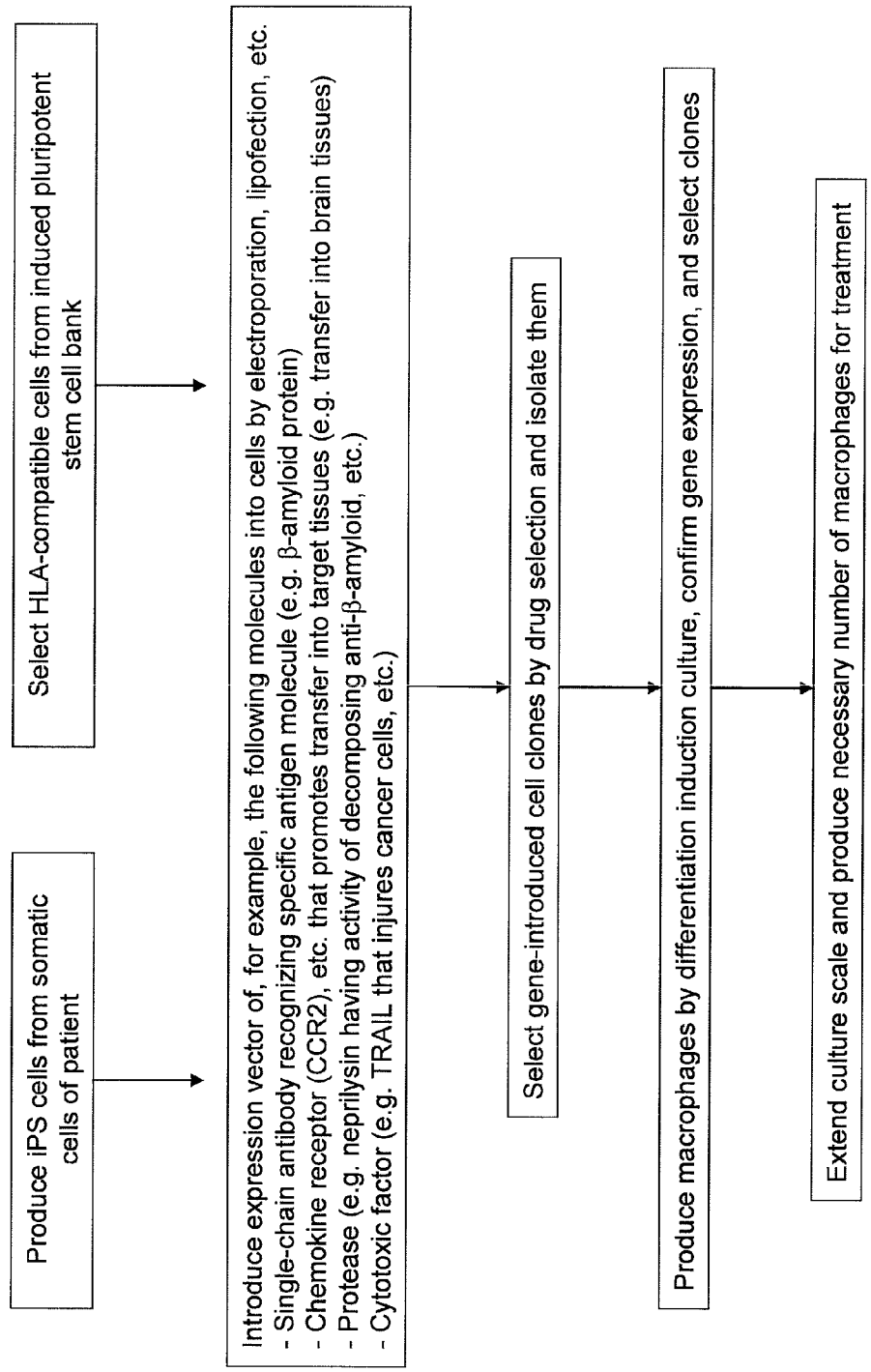
Figure 1. Method for producing cellular agent from genetically modified induced pluripotent stem cells Figure 2. Nucleotide sequences of single-chain antibody variable fragments (scFv) that recognize human β-amyloid peptides Leader peptide region (SEQ ID NO: 1)
ATGAACTTCGGGCTCAGCTTGATTTTCCTTGTCCTTGTTTTAAAAGGTGT
CCAGTGT Immunoglobulin heavy chain region (SEQ ID NO: 2)
GAAGTGAAGCTGGTGGAGTCTGGGGGAGGCTTAGTGAAGCCTG
GAGCGTCTCTGAAACTCTCCTGTGCAGCCTCTGGATTCACTTTCAGTAAC
TATGGCATGTCTTGGGTTCGCCAGAATTCAGACAAGAGGCTGGAGTGGGT
TGCATCCATTAGGAGTGGTGGTAGAGAGAATGCCAAGAACACCCTGTACCTG
AGGGCCGATTCACCATCTCCAGAGAGAATGCCAAGAACACCCTGTACCTG
CAAATGAGTAGTCTGAAGTCTGAGGACACGGCCTTGTATTATTGTGTCAG
ATATGATCACTATAGTGGTAGCTCCGACTACTGGGGCCAGGGCACCACT Linker peptide region (SEQ ID NO: 3)
GTCACCGTCTCCTCA
GGTGGAGGCGGTTCAGGCGGAGGTGGCTCTGGCGGTGGCGGATCG Immunoglobulin light chain region (SEQ ID NO: 4)
TATGTTGTGATGACCCAGACTCCACTCACTTTGTCGGTTA
CCATTGGACAACCAGCCTCCATCTCTTGCAAGTCAAGTCAGAGCCTCTTA
GATAGTGATGGAAAGACATATTTGAATTGGTTGTTACAGAGGCCAGGCCA
GTCTCCAAAGCGCCTAATCTATCTGGTGTCTAAACTGGACTCTGGAGTCC
CTGACAGGTTCACTGGCAGTGGGATCAGGGACAGATTTTACACTGAAAATC
AGCAGAATAGAGGCTGAGGATTTGGGACTTTATTATTGCTGCAAGGTAC
ACATTTCCTCGGACGTTCGGTGGAGGCACCAAGCTGGAAATCAAA Linker peptide region (SEQ ID NO: 5)
GCGGCCGCCGGGCCGGGGAGGAGGATCT Myc-Tag region (SEQ ID NO: 6)
gaacaaaaactcatctcagaagaggatctggtgccagggat Figure 3. Amino acid sequences of single-chain antibody variable fragments (scFv) that recognize human β-amyloid peptides Leader peptide (SEQ ID NO: 7)
MNFGLSLIFLVLVLKGVQC

Immunoglobulin heavy chain (SEQ ID NO: 8)
**EVKLVESGGGLVKPGASLKLSCAASGFTFSNYGMSWVRQNSDKRLEWVASIRSGGGRTYYSDNVKG
RFTISRENAKNTLYLQMSSLKSEDTALYYCVRYDHYSGSSDYWGQGTTVTVSS**

Linker peptide (SEQ ID NO: 9)
GGGGSGGGGSGGGGS

Immunoglobulin light chain (SEQ ID NO: 10)
**YVVMTQTPLTLSVTIGQPASISCKSSQSLLDSDGKTYLNWLLQRPGQSPKRLIYLVSKLDSGVPDRFTG
SGSGTDFTLKISRIEAEDLGLYYCWQGTHFPRTFGGGTKLEIK**

Linker peptide (SEQ ID NO: 11)
AAAGGGGS

Myc-Tag region (SEQ ID NO: 12)
EQKLISEEDLVPRD

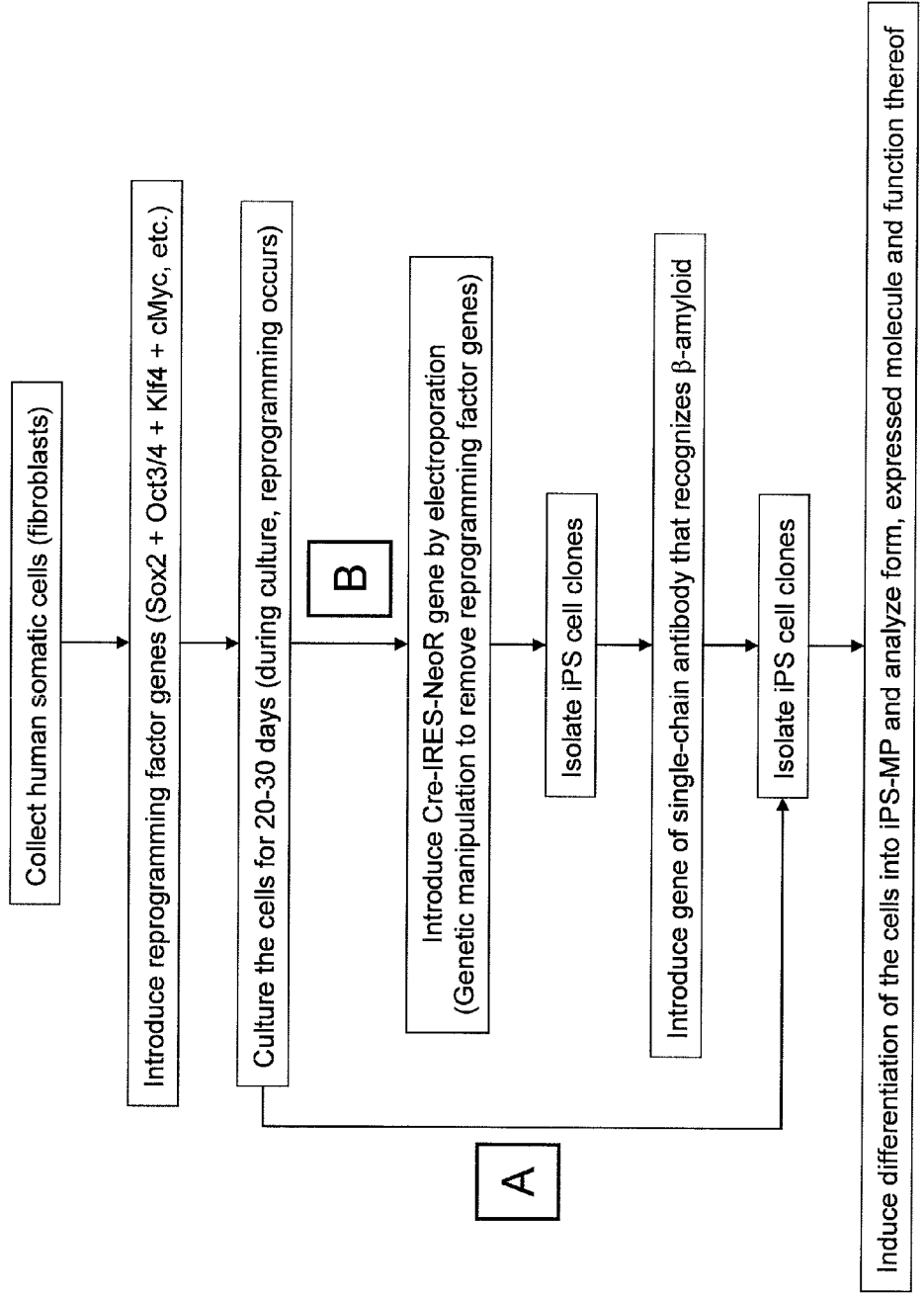
Figure 4. Summary of production and genetic modification of human iPS cells and production of iPS-MP Figure 5. Form of macrophages derived from human induced pluripotent stem cells
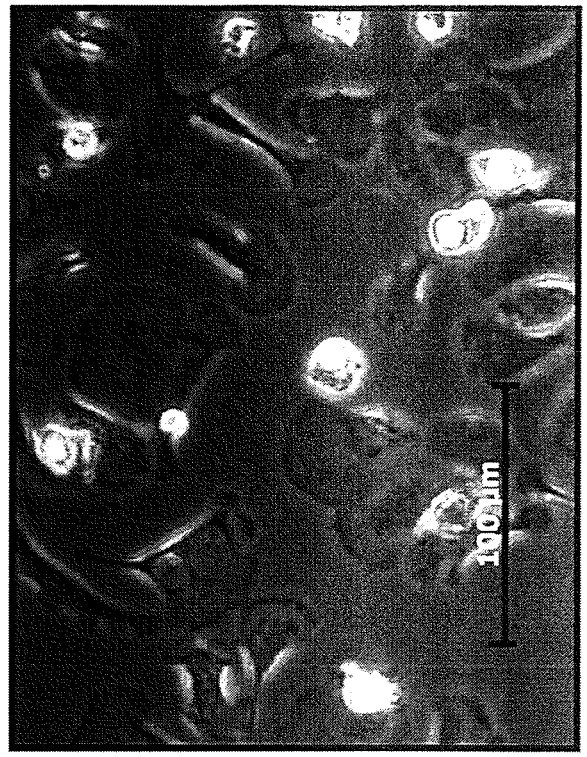
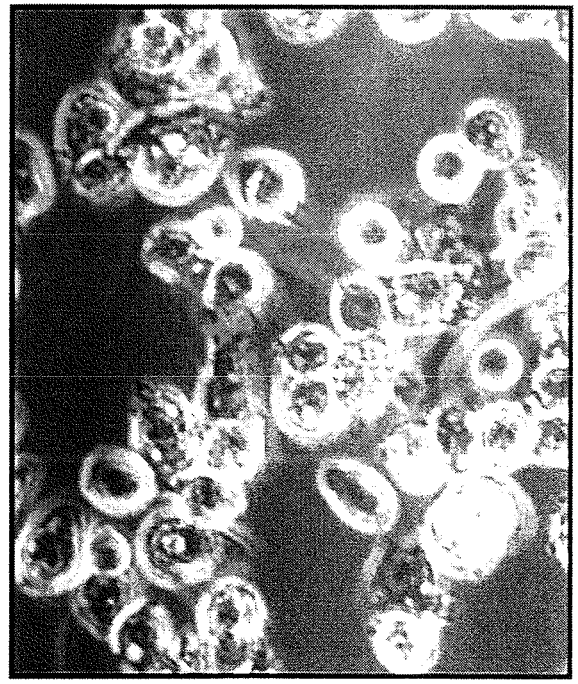

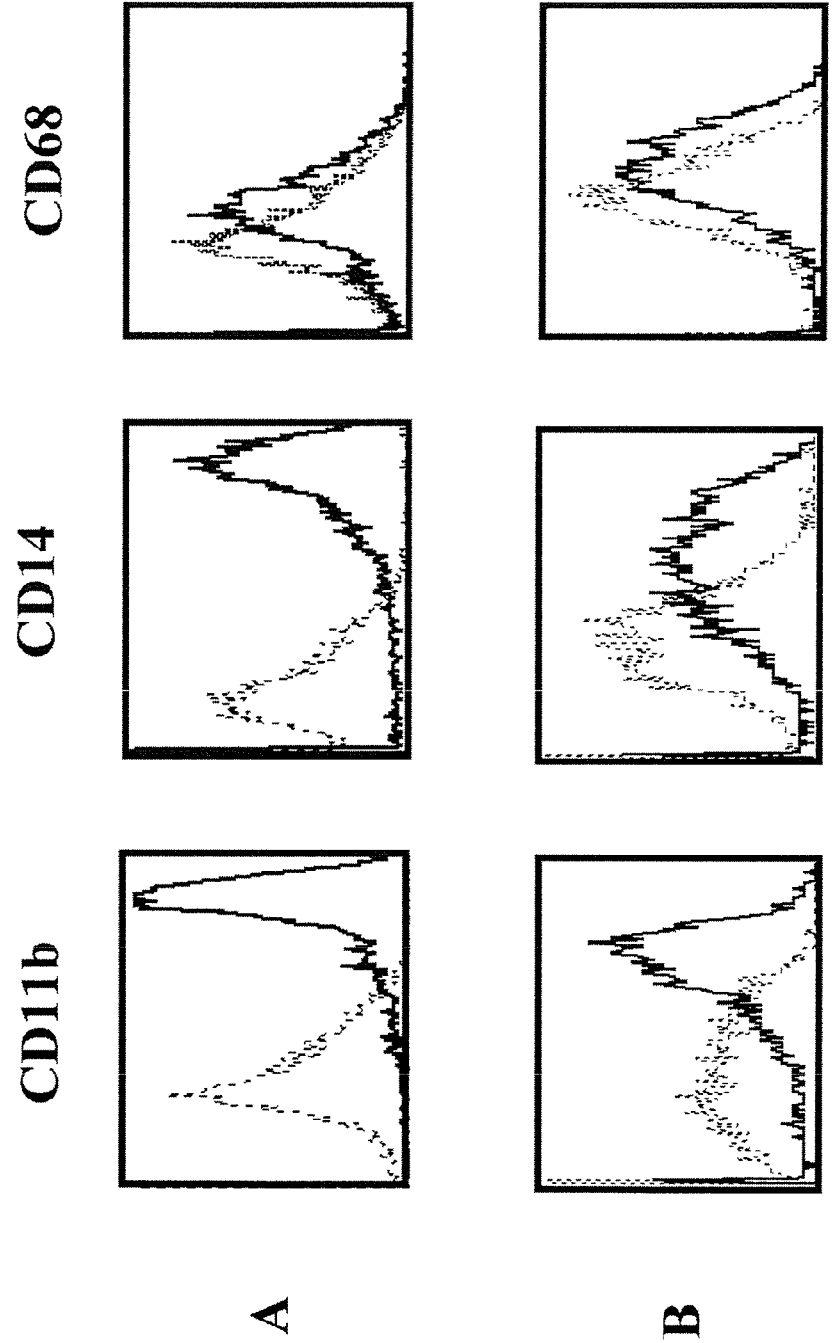
Figure 6. Expression of cell surface molecules in iPS-MP

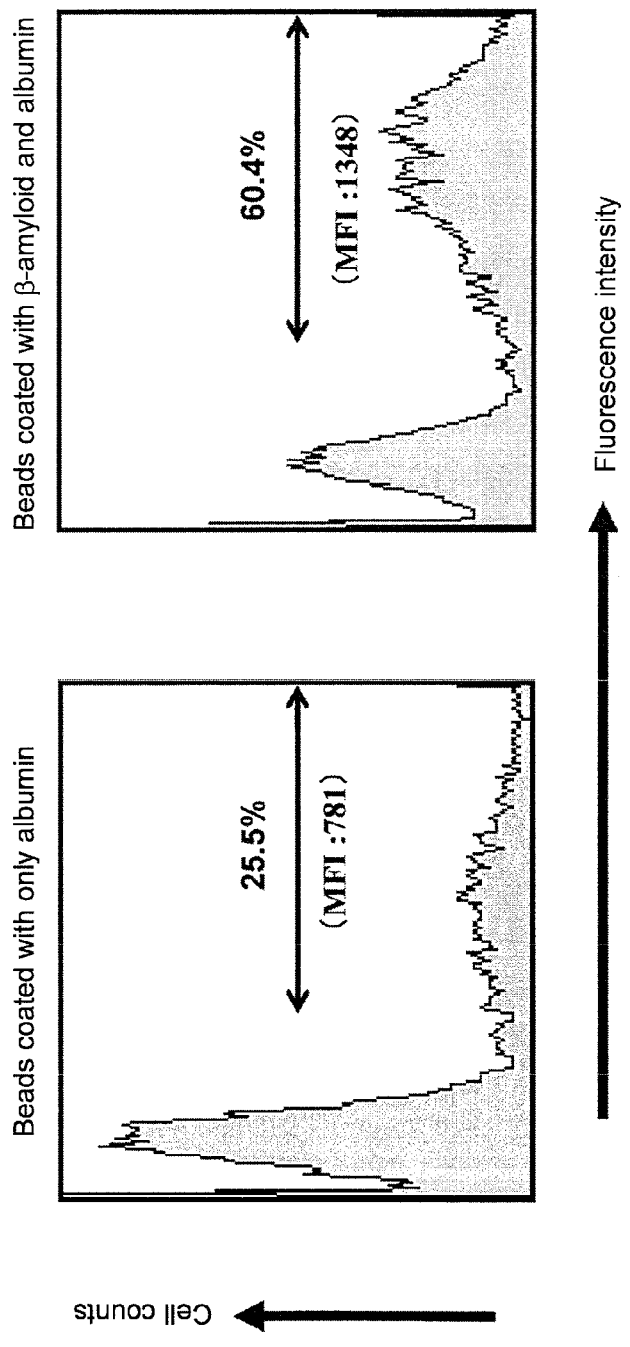
Figure 7. Phagocytosis of β-amyloid-coated fluorescent particles by macrophages expressing β-amyloid-specific single-chain antibody derived from induced pluripotent stem cells Figure 8. Microscopic images of iPS-MP expressing single-chain antibody directed against β-amyloid, which performed phagocytosis on β-amyloid-coated fluorescent beads
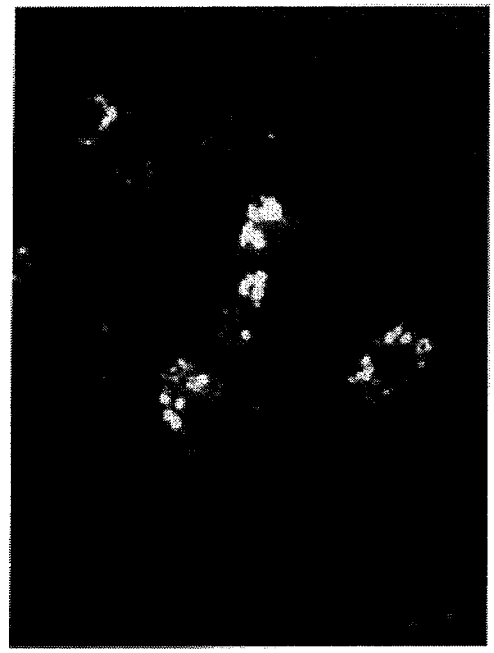
Fluorescent microscopic observation image
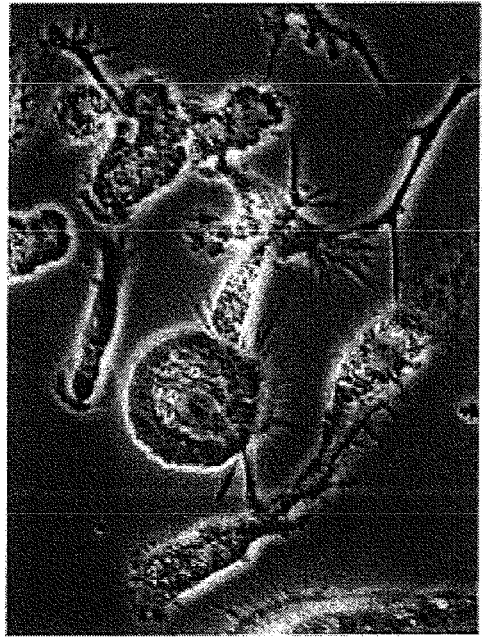
Phase-contrast microscopic observation image

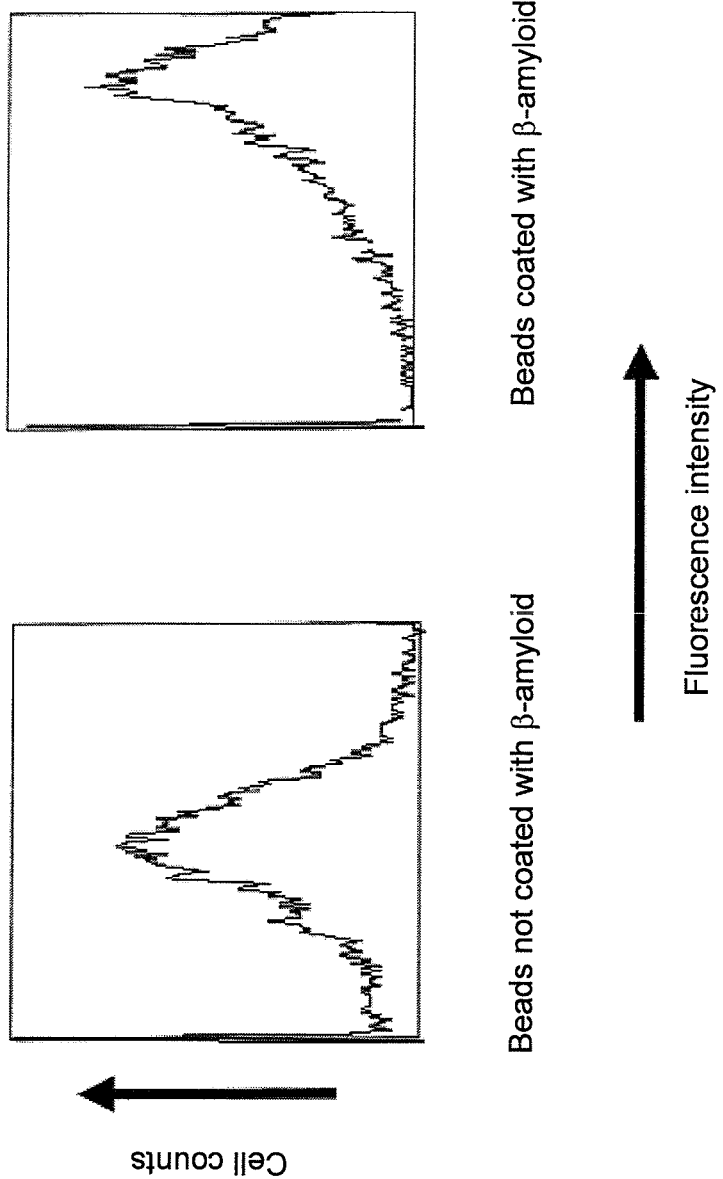
Figure 9. Specific phagocytosis of β-amyloid-coated beads by iPS-MP expressing single-chain antibody directed against β-amyloid (Analysis by flow cytometry)

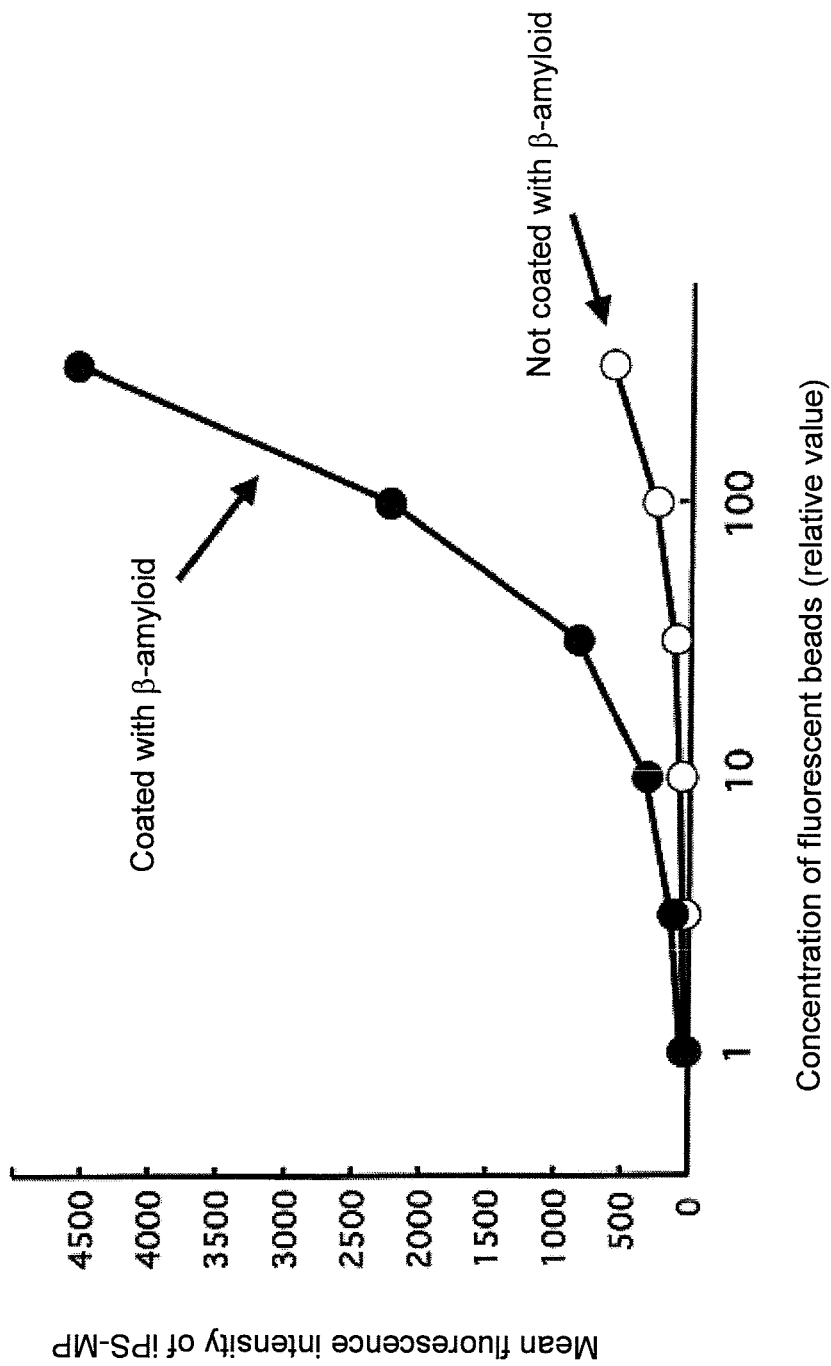
Figure 10. Specific phagocytosis of β-amyloid-coated beads by genetically modified iPS-MP in adhering state (Analysis by flow cytometry)

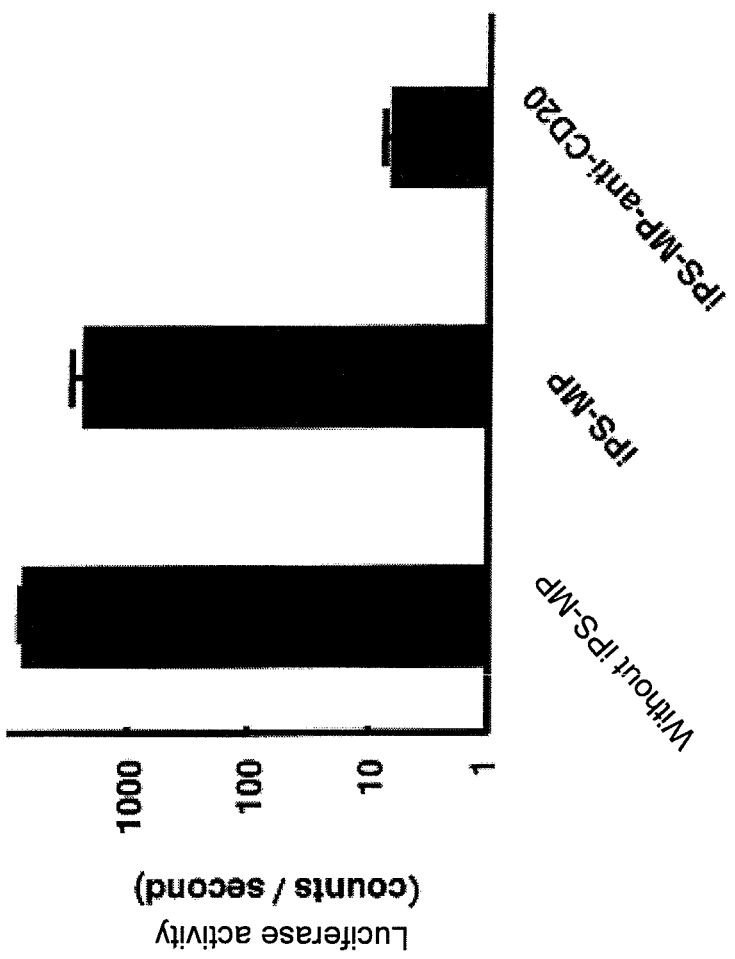
Figure 11. Suppressive effect of iPS-MP expressing antibody directed against CD20 on human leukemia cell line BALL-1 (Analysis in culture plate)

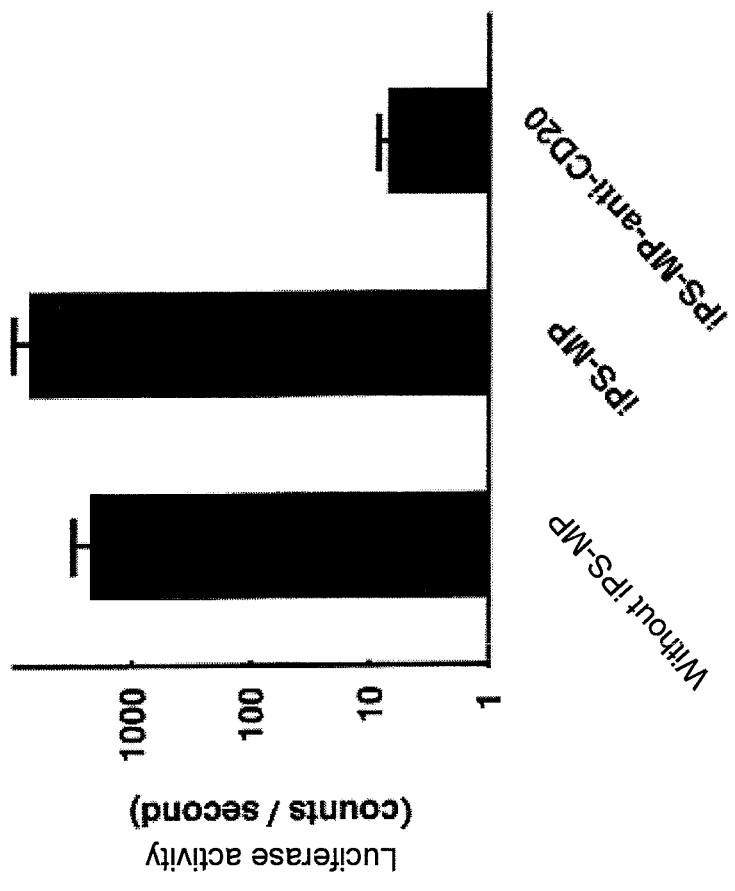
Figure 12. Effect of iPS-MP expressing antibody directed against CD20 on human leukemia cell line BALL-1 (Analysis in experiment regarding transplantation into scid mice)

SEQUENCE LISTING

```
<160> NUMBER OF SEQ ID NOS: 12

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgaacttcg ggctcagctt gattttcctt gtccttgttt taaaaggtgt ccagtgt      57

<210> SEQ ID NO 2
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaagtgaagc tggtggagtc tgggggaggc ttagtgaagc ctggagcgtc tctgaaactc      60
tcctgtgcag cctctggatt cactttcagt aactatggca tgtcttgggt tcgccagaat     120
tcagacaaga ggctggagtg ggttgcatcc attaggagtg gtggtggtag aacctactat     180
tcagacaatg taaagggccg attcaccatc tccagagaga tgccaagaa cacccctgtac      240
```

```
ctgcaaatga gtagtctgaa gtctgaggac acggccttgt attattgtgt cagatatgat    300
cactatagtg gtagctccga ctactggggc cagggcacca ct                      342
```

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
gtcaccgtct cctcaggtgg aggcggttca ggcggaggtg gctctggcgg tggcggatcg    60
```

<210> SEQ ID NO 4
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tatgttgtga tgacccagac tccactcact ttgtcggtta ccattggaca accagcctcc    60
atctcttgca agtcaagtca gagcctctta gatagtgatg aaagacata tttgaattgg    120 ttgttacaga ggccaggcca gtctccaaag cgcctaatct atctggtgtc taaactggac    180
tctggagtcc ctgacaggtt cactggcagt ggatcaggga cagattttac actgaaaatc    240
agcagaatag aggctgagga tttgggactt tattattgct ggcaaggtac acatttcct    300 cggacgttcg gtggaggcac caagctggaa atcaaa                             336
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gcggccgccg gcggaggagg atct                                           24
```

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gaacaaaaac tcatctcaga agaggatctg gtgcccaggg at                      42
```

<210> SEQ ID NO 7
<211> LENGTH: 19
<212> TYPE: PRT
<213> ORGANISM: Homo sapiens

<400> SEQUENCE: 7

```
Met Asn Phe Gly Leu Ser Leu Ile Phe Leu Val Leu Val Leu Lys Gly
1               5                   10                  15

Val Gln Cys
```

<210> SEQ ID NO 8
<211> LENGTH: 119
<212> TYPE: PRT
<213> ORGANISM: Homo sapiens

<400> SEQUENCE: 8

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Asn Ser Asp Lys Arg Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Thr Val Thr Val Ser Ser
            115

<210> SEQ ID NO 9
<211> LENGTH: 15
<212> TYPE: PRT
<213> ORGANISM: Homo sapiens

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 112
<212> TYPE: PRT
<213> ORGANISM: Homo sapiens

<400> SEQUENCE: 10

Tyr Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 11
<211> LENGTH: 8
<212> TYPE: PRT
<213> ORGANISM: Homo sapiens

<400> SEQUENCE: 11

Ala Ala Ala Gly Gly Gly Gly Ser

```
-continued

<210> SEQ ID NO 12
<211> LENGTH: 14
<212> TYPE: PRT
<213> ORGANISM: Homo sapiens

<400> SEQUENCE: 12

Glu Gln Lys Leu Ile Ser Glu Glu Asp Leu Val Pro Arg Asp
1               5                   10
```

METHOD OF MAKING MACROPHAGE EXPRESSING AN ANTIBODY DIRECTED AGAINST β-AMYLOID

The instant application contains a Sequence Listing which has been submitted in ASCII format via EFS-Web and is hereby incorporated by reference in its entirety. Said ASCII copy, created on Nov. 29, 2011, is named P40952.txt and is 5,356 bytes in size.

TECHNICAL FIELD

The present invention relates to a method for producing a cell medicine using induced pluripotent stem cells. More specifically, the present invention relates to a method for producing blood cells (macrophages) having phagocytic ability, which comprises performing genetic modification on induced pluripotent stem cells and then inducing differentiation of the resultant cells in vitro. The cell medicine (macrophage) produced by the method of the present invention expresses an antibody directed against a specific molecule and the like, as a result of gene introduction. The present cell medicine has a function to specifically recognize a target molecule so as to perform phagocytosis on and/or decompose the target molecule, or to specifically perform phagocytosis on and/or damage a cell expressing the target molecule, and other functions. It is anticipated that the cell medicine of the present invention will be useful for the treatment of diseases such as Alzheimer's disease, cancer, prion disease, and amyloidosis.

BACKGROUND ART

Induced pluripotent stem cell (iPS cell) means a cell having pluripotency, which is obtained by reprogramming a somatic cell. Several groups including the group of Professor Shinya Yamanaka et al. of Kyoto University, the group of Rudolf Jaenisch et al. of Massachusetts Institute of Technology, the group of James Thomson et al. of the University of Wisconsin, and the group of Konrad Hochedlinger et al. of Harvard University have succeeded in producing such induced pluripotent stem cells. The induced pluripotent stem cells have attracted great interest as ideal pluripotent cells having neither immunological rejections nor ethical issues. For example, International Publication WO2007/069666 describes nuclear reprogramming factors for somatic cells that include the gene products of Oct family gene, Klf family gene and Myc family gene, and nuclear reprogramming factors for somatic cells that include the gene products of Oct family gene, Klf family gene, Sox family gene and Myc family gene. This publication also describes a method for producing induced pluripotent stem cells by nuclear reprogramming of somatic cells, which comprises a step of allowing the aforementioned nuclear reprogramming factors to come into contact with somatic cells.

The induced pluripotent stem cells can be produced using, as materials, somatic cells such as human skin fibroblasts or blood cells, regardless whether such somatic cells are derived from a healthy person or a patient. As with embryonic stem cells (ES cells), the induced pluripotent stem cells have a latent capacity to differentiate into all types of cells, and also, they are able to grow inexhaustibly if they are cultured under appropriate conditions. Moreover, the induced pluripotent stem cells are cells on which gene introduction can be easily carried out by applying a method such as electroporation. On the other hand, since production of the induced pluripotent stem cells does not require human embryo, it can be apart from an ethical problem which poses an impediment to the use of embryonic stem cells. Today, a new method for producing induced pluripotent stem cells has been developing, and it is anticipated that a more efficient technique of producing induced pluripotent stem cells, has low risk when used, will be developed in the future.

Alzheimer's disease is a disease whereby progressive functional damage and deciduation occur in nerve cells in the brain, and this is a causative disease of many dementia cases. In addition, the risk of developing this disease increases with aging, and thus it is predicted that, in the future, this disease will cause socially and medical-economically more serious problems in various countries in which the population ages. At present, there are no effective therapeutic methods that are able to suppress the progression of this disease, and thus, it is strongly desired to develop a method for treating Alzheimer's disease based on elucidation of the mechanism for the development of this disease. Senile plaques found in the brain tissues in the autopsy case of Alzheimer's disease comprise, as a main ingredient, a polymerized β-amyloid peptide (Aβ1-42) generated as a result of limited degradation of an amyloid precursor protein (APP). With regard to the mechanism for the development of this disease, numerous findings that have been obtained so far indicate that it is most widely believed that a β-amyloid peptide that forms an oligomer or a large number of β-amyloid peptides that are polymerized and become insolubilized are causative substances that cause the functional damage and deciduation of nerve cells. One reason for an increased risk of developing the disease together with aging is that the expression level of protease assuming a role in decomposition of β-amyloid, such as neprilysin in local sites decreases together with aging, so that the balance between generation and decomposition is disrupted. Taking into consideration such a mechanism for the development of the disease, if a β-amyloid peptide can be decomposed or eliminated by some method, it is anticipated that such a method can be applied as an effective method for treating this disease. Although intensive studies have been conducted to develop an agent for decomposing β-amyloid or suppressing the generation thereof; there have not yet been developed any agents whose effects could be confirmed as of the present time.

A therapeutic method of removing a β-amyloid peptide via an immune response has also been studying, In an experiment in which Alzheimer's disease model mice were used, a β-amyloid peptide was administered as a vaccine to the mice, and an immune response to this vaccine was then induced. As a result, it was found that accumulation of the β-amyloid peptide and neurological symptoms could be suppressed. On the basis of these results, a clinical test regarding vaccine therapy was carried out. However, since encephalitis was provoked in some cases, this test was suspended. Recently, the results of a follow-up study of a case, in which a vaccine had been administered before the suspension of a clinical test, have been reported. Even in such a vaccine administration case, significant clinical effects were not obtained by the vaccine administration. It has been reported that the onset of the disease can be suppressed by administering a monoclonal antibody directed against a β-amyloid peptide to Alzheimer's disease model mice in an experiment using the mice. On the basis of these results, there has been performed a clinical test in which a monoclonal antibody directed against a β-amyloid peptide has been administered to patients. However, significant clinical effects have not yet been obtained as of the present time.

Moreover, it has also been known that an aggregate of abnormal proteins causes neuronal death in neurodegenerative diseases other than Alzheimer's disease. Examples of such neurodegenerative diseases include prion disease, Parkinson's disease, and amyotrophic lateral sclerosis (ALS). Furthermore, in so-called polyglutamine disease including Huntington's chorea as a typical example, neuronal death is caused by aggregation of polyglutamine proteins. Amyloidosis is a disease whereby an abnormal protein called amyloid is deposited and it causes the dysfunction of organs. Familial amyloid neuropathy is a representative example of systemic amyloidosis in which amyloid is systemically deposited in many organs. In such familial amyloid neuropathy, abnormal transthyretin proteins are generated and accumulated due to abnormality in a transthyretintransthyretin gene, and as a result, dysfunction is developed in various types of organs, such as peripheral neuropathy and autonomic neuropathy, are developed. There are no effective therapeutic methods for many diseases caused by such abnormal protein accumulation under the present circumstances. As in the case of Alzheimer's disease, if abnormal proteins that cause the onset of the diseases can be removed or decomposed, it is anticipated that such means can become an effective therapeutic method.

Neither surgical excision nor radiotherapy is effective for solid cancer having multiple metastasis foci and malignant tumor such as leukemia. If effective chemotherapeutics cannot be found, the disease is untreatable. Recently, as a new method for treating cancer, an antibody therapy, namely, a method of administering a monoclonal antibody that specifically recognizes a molecule expressed on the surface of a cancer cell (a cancer cell surface antigen) has been developed. Specifically, a therapeutic method of administering a monoclonal antibody directed against HER2 expressed on the breast cancer cell surface is a standard treatment for breast cancer. Moreover, for B cell lymphoma that accounts for 70% to 80% of all types of malignant lymphoma, an antibody therapy for administering a monoclonal antibody directed against a CD20 antigen expressed on B cells has been established. As a mode of action of such antibody therapy, there has been known antibody-dependent cellular cytotoxicity (ADCC), in which immunocytes (macrophages or natural killer cells) that express a Fc receptor (a receptor that binds to a Fc portion which is a constant region of an antibody) at a high level attack cancer cells, on the surface of which an antibody binds. Since antibody-dependent cellular cytotoxicity depends on the functions of immunocytes that are originally present in a body, whether or not a sufficient functional level of or a sufficient number of immunocytes are present in a body becomes one factor that influences the effectiveness of the treatment. In general, it has been known that the functions of immunocytes often decrease in cancer patients. It is considered that a macrophage, which specifically recognizes a cancer cell and then performs phagocytosis on or attacks it, can be produced by introducing a gene of an antibody directed against a cancer cell surface antigen into a macrophage. However, the number of macrophages or monocytes as precursor cells thereof, which can be separated from a human body, is limited, and artificial gene introduction into these cells is not easy.

Patent Document 2 describes: a method of differentiating the embryonic stem cells of a primate into dendritic cells; a method of producing dendritic cells from the embryonic stem cells of a primate; dendritic cells obtained by the aforementioned production method; use of the dendritic cells for the production of a pharmaceutical agent for treating diseases, on which the therapeutic effects can be obtained by antigen-specifically controlling immune response; and a cell medicine used for the treatment of the above-mentioned diseases.

PRIOR ART DOCUMENTS

Patent Documents

Patent Document 1: International Publication WO 2007/069666
Patent Document 2: International Publication WO 2006/022330

SUMMARY OF INVENTION

Object to be Solved by the Invention

It is an object of the present invention to provide a method for producing a cell medicine that is effective for diseases, to which no effective therapeutic methods have been developed to date, such as Alzheimer's disease, prion disease, amyloidosis, advanced cancer having a metastatic focus, and leukemia for which chemotherapy is ineffective, while causing a low risk to these diseases.

Means for Solving the Object

As a result of intensive studies directed towards achieving the aforementioned object, the present inventor has found that a phagocyte that expresses a foreign protein can be produced by introducing a protein expression vector into an induced pluripotent stem cell, and then inducing the protein expression vector-introduced induced pluripotent stem cell to differentiate into a phagocyte. Thus, the present invention has been completed.

According to the present invention, the following invention is provided.
(1) A method for producing a phagocyte that expresses a foreign protein, which comprises: a step of introducing a protein expression vector into an induced pluripotent stem cell; and a step of inducing the induced pluripotent stem cell, into which the protein expression vector has been introduced, to differentiate into a phagocyte.
(2) The method according to (1), wherein the induced pluripotent stem cell is a cell which is obtained by introducing a reprogramming factor into a somatic cell.
(3) The method according to (1) or (2), wherein the induced pluripotent stem cell is a cell which is obtained by introducing an Oct3/4 gene, a Klf4 gene, a Sox2 gene and a c-Myc gene into a somatic cell.
(4) The method according to (2) or (3), wherein the somatic cell is a human somatic cell.
(5) The method according to any one of (1) to (4), wherein the protein expressed by the protein expression vector is an antibody, a protease or a cytotoxic factor.
(6) The method according to any one of (1) to (5), wherein the protein expressed by the protein expression vector is an antibody directed against a β-amyloid peptide or an antibody directed against a molecule expressed on the surface of a tumor cell.
(7) The method according to any one of (1) to (6), wherein the protein expression vector is a plasmid vector.
(8) The method according to any one of (1) to (7), wherein the protein expression vector is a vector comprising a drug resistance gene.
(9) The method according to any one of (1) to (8), wherein the step of inducing the induced pluripotent stem cell, into which the protein expression vector has been introduced, to differentiate into a phagocyte, comprises culturing a cell derived from the induced pluripotent stem cell in the presence of a granulocyte-macrophage colony-stimulating factor (GM-CSF) and/or a macrophage colony-stimulating factor (M-CSF).

(10) The method according to any one of (1) to (9), wherein the step of inducing the induced pluripotent stem cell, into which the protein expression vector has been introduced, to differentiate into a phagocyte, comprises:

(A) a step of allowing the induced pluripotent stem cell, into which the protein expression vector has been introduced, to differentiate into a cell group A containing mesodermal cells; and (B) a step of co-culturing the cell group A obtained in the step (A) in the presence of a granulocyte-macrophage colony-stimulating factor (GM-CSF), so as to obtain a cell group B of myeloid blood cells (macrophages) having phagocytic ability.

(11) A phagocyte produced by the method according to any one of (1) to (10).

(12) A cell medicine which comprises a phagocyte produced by the method according to any one of (1) to (10).

(13) The cell medicine according to (12), which is a cell medicine for treatment and/or prevention of neurodegenerative disease or malignant tumor.

Advantageous Effects of Invention

The establishment of induced pluripotent stem cells and production of phagocytes (macrophages) by in vitro induction of differentiation from the induced pluripotent stem cells according to the present invention are not influenced by the internal environment of a patient, such as abnormality in immunocompetent cells in a cancer-bearing state or a reduction in hematopoietic ability. Moreover, induced pluripotent stem cells can be produced in large numbers by culturing them under suitable conditions so as to allow them to grow. Using the thus obtained induced pluripotent stem cells as materials, phagocytes can be produced in large numbers, and also, genetic modification can easily be carried out. Accordingly, by applying a technique of producing phagocytes (macrophages) from induced pluripotent stem cells, using the induced pluripotent stem cells as materials, a cell medicine useful for the treatment of various types of diseases such as Alzheimer's disease and cancer can be stably produced in a large amount, as necessary.

BRIEF DESCRIPTION OF DRAWINGS

FIG. 1 shows a summary of the method of the present invention for producing a cell medicine used for the treatment of various types of diseases from induced pluripotent stem cells. The induced pluripotent stem cells may be derived from the somatic cells of a patient. Otherwise, suitable cells may be selected from an induced pluripotent stem cell bank that covers various types of HLA (human leukocyte antigen) types, which will be established in the future, and the selected cells may be used as induced pluripotent stem cells.

FIG. 2 shows nucleotide sequences that correspond to single-chain antibody variable fragments (scFv) which recognize β-amyloid protein. These are the nucleotide sequences of single-chain antibody variable fragments (scFv) recognizing β-amyloid proteins which comprises leader peptide region. The sequences of the heavy and light chains are derived from the sequence of a mouse hybridoma clone 3D6. There is a linker sequence between the heavy and light chains. For the purpose of confirming the expression of a molecule derived from a vector in a cell on which gene introduction has been performed by flow cytometric analysis, a cMyc-Tag sequence, as well as the linker sequence, is ligated to a site downstream of the light chain.

FIG. 3 shows the nucleotide sequences of an immunoglobulin Fc portion and a mouse Fc receptor trans-cell membrane-cytoplasm portion. FIG. 3 shows the amino acid sequences of proteins encoded by the nucleotide sequences shown in FIG. 2.

FIG. 4 shows a summary of the production and genetic modification of human iPS cells and the production and analysis of iPS-MP, which were conducted in Examples.

FIG. 5 shows the phase-contrast microscopic images of macrophages derived from human iPS cells (iPS-MP). FIG. 5A shows the form of iPS-MP, into which a scFv gene has not been introduced. FIG. 5B shows the form of iPS-MP, into which a gene of a single-chain antibody (scFv) directed against a β-amyloid protein has been introduced after c-myc and Sox2 genes acting as reprogramming factors had been removed by introduction of a Cre expression vector.

FIG. 6 shows the results obtained by analyzing the expression of a cell surface molecule in iPS-MP by flow cytometry. FIG. 6A shows the expression of a marker molecule on the cell surface of iPS-MP derived from a human iPS cell, into which a scFv gene has not been introduced. FIG. 6B shows the expression of a marker molecule on the cell surface of iPS-MP derived from a human induced pluripotent stem cell, into which a scFV gene directed against a β-amyloid protein has been introduced. The iPS-MP was stained with a fluorescently-labeled monoclonal antibody directed against macrophage marker molecules (CD11b, CD14 and CD68), and it was then analyzed by flow cytometry. The horizontal axis of a histogram indicates fluorescence intensity, and the longitudinal axis thereof indicates cell counts. The figures show the results obtained by staining the iPS-MP with a monoclonal antibody specific to each molecule (bold solid line) and the results obtained by staining an irrelevant antibody (isotype control antibody) having the same isotype as that of each antibody (thin dotted line).

FIG. 7 shows the phagocytosis of β-amyloid-coated fluorescent particles by iPS-MP expressing a single-chain antibody directed against a β-amyloid protein. The figure shows the results obtained by allowing iPS-MP that expresses a single-chain antibody directed against a human β-amyloid protein to react with fluorescent particles that have been coated with β-amyloid (right: coated with a human β-amyloid protein and albumin), or have not been coated with (i-amyloid (left: coated with only albumin), and then analyzing the phagocytic level of the fluorescent particles by the iPS-MP by flow cytometry. It is found that, by coating the fluorescent particles with β-amyloid, larger counts of cells perform phagocytosis on the beads (25.5→60.3%), and the number of beads englobed by a single cell increases (mean fluorescence intensity: 781→1348). Such an increase in phagocytic activity specific to β-amyloid was observed only in the case of iPS-MP that expressed a single-chain antibody specific to β-amyloid.

FIG. 8 shows microscopic images of iPS-MP expressing a single-chain antibody directed against β-amyloid that performed phagocytosis on fluorescent beads coated with β-amyloid. The left image shows a bright field image photographed using a phase-contrast lens, and it indicates the form of the iPS-MP. The right image shows a fluorographic image. It shows localization of fluorescent beads and also shows that the fluorescent beads have been incorporated into the cell of iPS-MP.

FIG. 9 shows specific phagocytosis of β-amyloid-coated beads by iPS-MP expressing a single-chain antibody directed against β-amyloid (analysis by flow cytometry). The left panel shows the analysis results of iPS-MP, to which beads that had not been coated with β-amyloid have been added. The right panel shows the analysis results of iPS-MP, to which β-amyloid-coated beads have been added.

FIG. 10 shows specific phagocytosis of β-amyloid-coated beads by genetically modified iPS-MP in an adhering state (analysis by flow cytometry). A graph is made from mean values of the fluorescence intensity of the iPS-MP that are obtained by changing the concentration of the beads added to the iPS-MP. The open circle indicates a case in which beads that had not been coated with β-amyloid have been added, and the filled circle indicates a case in which β-amyloid-coated beads have been added. The horizontal axis of the graph indicates the concentration of the beads added to the iPS-MP, and the longitudinal axis thereof indicates the fluorescence intensity of the cells after recovery.

FIG. 11 shows the suppressive effect of iPS-MP expressing an antibody directed against CD20 on a human leukemia cell line BALL-1. When compared with a case in which only BALL-1 cells were cultured, or when compared with a case in which iPS-MP that did not express a CD20-specific single-chain antibody was added to the BALL cells and the obtained mixture was then cultured, when iPS-MP expressing a CD20-specific single-chain antibody was added to the BALL cells and the obtained mixture was then cultured, luciferase activity was found to be 1/100 or less.

FIG. 12 shows the effect of iPS-MP expressing an antibody directed against CD20 on a human leukemia cell line BALL-1 (analysis in an experiment regarding transplantation of iPS-MP into scid mice). When compared with a group in which only BALL-1 cells were injected into the mice, or when compared with a group in which iPS-MP that did not express a CD20-specific single-chain antibody was added to the BALL cells and the obtained mixture was then cultured, in a group in which iPS-MP expressing a CD20-specific single-chain antibody was added to the BALL cells and the obtained mixture was then cultured, luciferase activity in the omental tissues was found to be 1/100 or less.

EMBODIMENTS FOR CARRYING OUT THE INVENTION

The present invention will be described more in detail below.

In the after-mentioned Examples of the present specification, a gene of an antibody directed against a specific molecule was introduced into induced pluripotent stem cells, and differentiation of the induced pluripotent stem cells was then induced in vitro, so as to produce phagocytes (macrophages). The thus produced phagocytes express an antibody directed against a specific molecule and the like, and these cells have activity of specifically recognizing a target molecule and performing phagocytosis on it. Not only a specific antibody but also protease or the like is allowed to simultaneously express in induced pluripotent stem cells, so as to produce phagocytes (macrophages) exhibiting the function to perform phagocytosis on and decompose a target molecule with high efficiency, or to specifically perform phagocytosis on and/or damage a cell that expresses a target molecule. FIG. 1 shows a summary of the method of the present invention for producing a cell medicine from induced pluripotent stem cells.

(1) Induced Pluripotent Stem Cell

The induced pluripotent stem cell used in the present invention can be produced by reprogramming a somatic cell. The type of the somatic cell used herein is not particularly limited. Any given somatic cell can be used. That is to say, the somatic cell according to the present invention includes all of cells constituting a living body, other than germ cells. The somatic cell of the present invention may be either a differentiated somatic cell or an undifferentiated stem cell. The origin of such a somatic cell is not particularly limited, and examples of such origin include mammals, birds, fishes, reptiles and amphibians. Of these, mammals (for example, rodents such as a mouse, or primates such as a human) are preferable. A human is particularly preferable. When the somatic cells of such a human are used, the somatic cells of any one of a fetus, a newborn child and an adult may be used. When the induced pluripotent stem cells produced by the method of the present invention are used in the treatment of a disease such as regenerative medicine, somatic cells separated from a patient suffering from the disease are preferably used.

The term "induced pluripotent stem cell" is used in the present invention to mean a stem cell, which has self-replication ability over a long period of time under certain culture conditions (e.g. conditions for culturing ES cells) and which has pluripotency to differentiate into ectoderm, mesoderm and endoderm under certain differentiation induction conditions. In addition, the induced pluripotent stem cell used in the present invention may also be a stem cell having ability to form a teratoma when it is transplanted into a test animal such as a mouse.

In order to produce induced pluripotent stem cells from somatic cells, at least one type of reprogramming gene is first introduced into the somatic cells. The reprogramming gene means a gene encoding a reprogramming factor having action to reprogram somatic cells and convert them to induced pluripotent stem cells. In the present invention, at least one type of reprogramming gene is used. Specific examples of a combination of reprogramming genes used in the present invention are given below. However, examples of such a combination are not limited thereto.

(i) Oct gene, Klf gene, Sox gene, and Myc gene
(ii) Oct gene, Sox gene, NANOG gene, and LIN28 gene
(iii) Oct gene, Klf gene, Sox gene, Myc gene, hTERT gene, and SV40 large T gene
(iv) Oct gene, Klf gene, and Sox gene The Oct gene, Klf gene, Sox gene and Myc gene each include multiple family genes. Specific examples of family genes of the aforementioned genes are described in pp. 11 to 13 of the specification of International Publication WO2007/069666, and such family genes can be used. Specific examples are as follows.

Specific examples of genes belonging to the Oct gene include Oct3/4 (NM_002701), Oct1A (NM_002697), and Oct6 (NM_002699) (the number shown in the parentheses indicates NCBI accession number of its human gene). A preferred example is Oct3/4. Oct3/4 is a transcriptional factor belonging to the POU family, and it is known as an undifferentiation marker. Also, it has been reported that Oct3/4 is associated with the maintenance of pluripotency.

Specific examples of genes belonging to the Klf gene include Klf1 (NM_006563), Klf2 (NM_016270), Klf4 (NM_004235), and Klf5 (NM_001730) (the number shown in the parentheses indicates NCBI accession number of its human gene). A preferred example is Klf4. Klf4 (Kruppel like factor-4) has been reported as a tumor suppressor.

Specific examples of genes belonging to the Sox gene include Sox1 (NM 005986), Sox2 (NM_003106), Sox3 (NM_005634), Sox7 (NM_031439), Sox15 (NM_006942), Sox17 (NM_0022454), and Sox18 (NM_018419)

(the number shown in the parentheses indicates NCBI accession number of its human gene). A preferred example is Sox2. Sox2 is a gene, which is expressed in the early development process and encodes a transcriptional factor.

Specific examples of genes belonging to the Myc gene include c-Myc (NM_002467), N-Myc (NM_005378), and L-Myc (NM_005376) (the number shown in the parentheses indicates NCBI accession number of its human gene). A preferred example is c-Myc. The c-Myc is a transcriptional regulator associated with differentiation and growth of cells, and it has also been reported that it is associated with the maintenance of pluripotency.

The above-described genes are commonly present in mammals including humans. In the present invention, a gene derived from any given mammal (for example, a gene derived from a mammal such as a human, a mouse, a rat or a monkey) can be used. Moreover, a mutant gene, which comprises a substitution, insertion and/or deletion of several (for example, 1 to 30, preferably 1 to 20, more preferably 1 to 10, further preferably 1 to 5, and particularly preferably 1 to 3) nucleotides with respect to a wild-type gene and which has the same function as that of the wild-type gene, can also be used.

In the present invention, a combination of the Oct3/4 gene, the Klf4 gene, the Sox2 gene and the c-Myc gene can be particularly preferably used as reprogramming genes.

The method of introducing a reprogramming gene into somatic cells is not particularly limited, as long as the introduced reprogramming gene can be expressed therein and can achieve the reprogramming of the somatic cells. For example, using an expression vector containing at least one type of reprogramming gene, the reprogramming gene can be introduced into somatic cells. When two or more types of reprogramming genes are introduced into somatic cells using a vector, two or more types of reprogramming genes may be incorporated into a single expression vector and the expression vector may be then introduced into the somatic cells. Alternatively, two or more types of expression vectors, into each of which one type of reprogramming gene has been incorporated, are prepared, and these expression vectors may be then introduced into the somatic cells.

The type of such an expression vector is not particularly limited. It may be either a viral vector or a plasmid vector. A viral vector is preferable. It is particularly preferably a viral vector such that the introduced reprogramming gene can be incorporated into the chromosomes of somatic cells. Examples of the viral vector that can be used in the present invention include a retrovirus vector (including a lentivirus vector), an adenovirus vector, and an adeno-associated virus vector. Of these, a retrovirus vector is preferable, and a lentivirus vector is particularly preferable.

As packaging cells used to produce a recombinant viral vector, any given cells can be used, as long as they are cells capable of supplying a lacked protein to a recombinant viral vector plasmid that lacks at least one gene encoding a protein necessary for the packaging of a virus. For example, there can be used packaging cells that are based on human kidney-derived HEK293 cells or mouse fibroblasts NIH3T3.

A recombinant viral vector can be produced by introducing a recombinant vial vector plasmid into packaging cells. The method of introducing the aforementioned viral vector plasmid into the aforementioned packaging cells is not particularly limited. Examples of the introduction method that can be used herein include known gene introduction methods such as a calcium phosphate method, lipofection or electroporation.

A medium capable of maintaining the undifferentiation potency and pluripotency of ES cells is known in the present technical field. The induced pluripotent stem cells of the present invention can be separated and cultured by using suitable media in combination. That is, examples of a medium for culturing the induced pluripotent stem cells of the present invention: an ES medium; and an MEF conditioned ES medium, which is a supernatant obtained by adding 10 ng/ml FGF-2 to the ES medium and then culturing mouse embryo fibroblasts therein for 24 hours (hereinafter referred to as an MEF conditioned ES medium). To the medium for culturing the induced pluripotent stem cells of the present invention, various types of growth factors, cytokine, hormone, and the like (for example, components associated with the growth and/or maintenance of human ES cells, such as FGF-2, TGFb-1, activin A, Nanoggin, BDNF, NGF, NT-1, NT-2 and NT-3) may be added. Moreover, the differentiation potency and proliferation potency of the separated induced pluripotent stem cells can be confirmed by utilizing a method of confirmation known for ES cells.

(2) Introduction of Protein Expression Vector into Induced Pluripotent Stem Cells In the present invention, a protein expression vector is introduced into induced pluripotent stem cells. The type of a protein which is expressed by the protein expression vector is not particularly limited. Examples of such a protein include an antibody (for example, a single-chain antibody) that recognizes a specific antigen molecule (for example, a β-amyloid protein and a CD20 molecule), a chemokine receptor (CCR2, etc.) that promotes transfer into target tissues (for example, transfer into brain tissues), protease (for example, neprilysin having activity of decomposing β-amyloid, and trypsinogen), and a cytotoxic factor (for example, TRAIL that injures cancer cells). As an antibody, an antibody directed against a protein or a peptide that becomes a target of the treatment can be used. For example, there can be used antibodies directed against a β-amyloid peptide in Alzheimer's disease, an aggregate of abnormal proteins in neurodegenerative disease, a protein specifically expressed in cancer cells (a tumor antigen protein), a peptide as a portion of such tumor antigen protein, etc.

A protein expression vector preferably comprises a drug resistance gene. As such drug resistance genes, genes that confer resistance to selective drugs such as G418, puromycin and hygromycin can be used. After completion of gene introduction, cells are cultured in a culture solution containing the above-mentioned selective drug, and cells into which the gene has been introduced are selected, so that gene-introduced cell clones can be isolated.

Such a protein expression vector can be introduced into cells according to a commonly used method such as electroporation or lipofection. Among the aforementioned methods, electroporation is desirable.

An expression vector, which is able to express a gene in mammalian cells including macrophages with high efficiency, is preferably used. Examples of the expression vector that can be used herein include a plasmid vector and a phage vector. The expression vector may comprise elements effective for promotion of transcription, such as various types of promoters, enhancers or terminators, as necessary.

(3) Induction of Differentiation of Induced Pluripotent Stem Cells into Phagocytes In the present invention, differentiation of induced pluripotent stem cells into phagocytes is induced by an in vitro differentiation induction method.

That is to say, the step of inducing differentiation of induced pluripotent stem cells, in which a protein expression vector has been introduced, into phagocytes is not particularly limited, as long as it is able to induce differentiation into phagocytes. For example, differentiation of the induced pluripotent stem cells into blood cells containing phagocytes can be induced by a co-culture method comprising culturing the induced pluripotent stem cells together with cells (feeder cells) having the property of inducing the differentiation and proliferation of blood cells. However, the differentiation induction methods applied in the present invention are not limited to this feeder cell co-culture method. For example, it is also possible to induce differentiation of the induced pluripotent stem cells without using feeder cells by culturing the induced pluripotent stem cells in a cell-adhesive culture vessel, the surface of which has been coated with fibronectin or the like. Otherwise, a cell mass of the induced pluripotent stem cells may be cultured in a suspending state so as to form an embryoid, and thereafter, it may be induced to differentiate into phagocytes. Considering that the induced pluripotent stem cells are administered as a cell medicine into a human body, a method of inducing differentiation without using feeder cells is more preferable.

The type of a culture solution used during induction of differentiation of the induced pluripotent stem cells into phagocytes is not particularly limited, as long as it is a culture solution suitable for the culture of mammalian cells. Such a culture solution can be selected, as appropriate, depending on the type of the induced pluripotent stem cells used. Examples of such a culture solution include αMEM, DMEM, and IMDM (Iscove's modified Dulbecco's medium).

The culture solution used in differentiation induction culture may be either a serum-containing culture solution or a serum-free culture solution. There is a serum-free culture solution, which does not contain any substance derived from the serum of a human or an animal other than the human. However, the serum-free culture solution used herein also includes a culture solution containing specific ingredients derived from the purified serum (e.g. albumin, etc.). The serum-free culture solution, which does not contain any substance derived from serum, may contain a protein produced by genetic recombination, such as insulin, a fatty acid, a microelement, and a surfactant, as appropriate. Taking into consideration the fact that the phagocyte is to be administered as a cell medicine to a human body, a serum-free culture solution is preferably used.

The type of a medium that can be used to produce feeder cells used for the co-culture with induced pluripotent stem cells in the present invention is not particularly limited, as long as it is suitable for the culture of adhesive mammalian cells. Such a medium may be selected, as appropriate, depending on the type of the cells used as feeder cells, etc. Examples of such a medium include αMEM and DMEM, [Dulbecco's modified Eagle's medium (culture solution)].

The type of a culture vessel used to induce the differentiation of induced pluripotent stem cells into phagocytes is not particularly limited, as long as such differentiation induction can be carried out therein. For instance, such differentiation induction can be carried out using a culture vessel made of polystyrene, whose cell adhesiveness has been enhanced by coating the surface thereof with gelatin, fibronectin or the like. However, examples of the culture vessel are not limited thereto. It is also possible to use a gas-permeable bag for cell culture, for example, for the purpose of aseptically preparing large quantities of cells.

Conditions for culturing the above-described feeder cells can be determined, as appropriate, depending on the type of the cells used as feeder cells. For example, in the case of ST2 cells, OP9 cells and the like, there are applied conditions in which the cells are cultured at 37° C. in a 5 vol % $CO_2$, in a medium to which 10 vol % fetal bovine serum has been added, on a culture vessel coated with a 0.1-weight-% gelatin solution or the like.

Gas atmosphere conditions for culture can be determined, as appropriate, depending on the type of induced pluripotent stem cells used, the composition of a culture solution, and the like. For example, there are applied conditions consisting of approximately 37° C. (in particular, 37° C.) and 5 vol % $CO_2$.

In order to induce the differentiation of induced pluripotent stem cells into phagocytes, the induced pluripotent stem cells can be preferably cultured in the presence of a granulocyte-macrophage colony-stimulating factor (GM-CSF) or a macrophage colony-stimulating factor (M-CSF). The content of the granulocyte-macrophage colony-stimulating factor (GM-CSF) in a medium is preferably within a range from 50 to 200 ng/ml.

According to the above-described method, phagocytes having properties as phagocytes (for example, the expression of CD11b, CD14 and CD68) can be obtained. The phagocytes which are produced by the method of the present invention have phagocytic activity on antigen proteins.

(4) Phagocyte and Cell Medicine of the Present Invention

The present invention further relates to a phagocyte produced by the above-described method and a cell medicine comprising the same. According to the phagocyte of the present invention, there can be provided a cell medicine, which has low risk and is effective for Alzheimer's disease, prion disease, amyloidosis, advanced cancer having a metastatic focus, and leukemia for which chemotherapy is ineffective.

When the cell medicine of the present invention is produced, auxiliary agents capable of stably retaining the phagocyte of the present invention, such as a medium, may be used, as appropriate.

According to the present invention, there is provided a method for treating a disease of a subject, which is characterized in that it comprises administering a therapeutically effective amount of the phagocyte obtained by the above-described production method to the subject.

The therapeutically effective amount means herein the amount of the phagocyte, which is able to provide therapeutic effects on the aforementioned disease of a subject when the phagocyte obtained by the above-described production method is administered to the subject, as compared with another subject to which the phagocyte is not administered. A specific therapeutically effective amount may be determined, as appropriate, depending on the dosage form of the phagocyte, an administration method, an intended use, and the age, body weight and symptoms of the subject. Thus, such a therapeutically effective amount cannot be categorically determined. For example, the therapeutically effective amount of the phagocyte is preferably 200,000 to 1,000,000 cells/kg of body weight, at cell counts of the phagocytes, per single treatment of a human (e.g. an adult).

Examples of the method for administering the cell medicine of the present invention include hypodermic injection, intralymphatic injection, intravenous injection, intraperitoneal injection, intrathoracic injection, and direct injection into a local site in which malignant tumor is present. However, examples of the administration method are not limited thereto.

The present invention will be more specifically described in the following examples. However, these examples are not intended to limit the scope of the present invention.

EXAMPLES

Example 1

Production of Single-Chain Antibody (ScFV) Expression Vector that Recognizes Human β-Amyloid Peptide (1) Production of Variable Region Nucleotide Sequences Based on the nucleotide sequences of the variable regions of the heavy chain and light chain of a monoclonal antibody recognizing a human β-amyloid peptide (mouse hybridoma clone: 3D6) (described in Patent document 2007-0238154), the nucleotide sequence of a single-chain antibody variable region recognizing a β-amyloid peptide was designed. FIG. 2 shows the nucleotide sequence thereof, and FIG. 3 shows the amino acid sequence of a protein encoded by this nucleotide sequence. Based on the designed nucleotide sequence, GeneScript Corporation (New Jersey, U.S.A.) was asked to artificially synthesize DNA. Thereafter, the synthesized DNA was inserted into a plasmid vector.

(2) Production of Immunoglobulin (Mouse IGG2a) Fc Portion and Mouse Fc Receptor (FcγRI) Trans-Cell Membrane-Cytoplasm Site Using cDNA derived from RNA extracted from the spleen tissue of C57BL/6 mice as a template, the aforementioned portion was produced by the PCR method.

(3) Production of Expression Vector of Fusion Protein of Single-Chain Antibody Recognizing β-Amyloid Peptide and Immunoglobulin Fc Portion and Fc Receptor (Fcγ Trans-Cell Membrane-Cytoplasm Site)

A DNA fragment of the above-described single-chain antibody variable region was fused with a DNA fragment of the immunoglobulin Fc portion and mouse Fc receptor trans-cell membrane-cytoplasm site according to the PCR method, and the fused product was then inserted into a plasmid vector (pENTR-D-TOPO; manufactured by Invitrogen). The obtained plasmid vector was cloned into *Escherichia coli*.

The nucleotide sequence of the cloned plasmid DNA was confirmed by sequence analysis, and the DNA was then introduced into a mammal expression vector using DNA recombinant enzyme LR clonase (manufactured by Invitrogen). As such a mammal expression vector, there was used pCAGGS-IRES-Puro that was a vector driven by a CAG promoter, into which IRES (internal ribosomal entry site) and a puromycin resistance gene had been incorporated.

Example 2

Production and Culture of Human Induced Pluripotent Stem Cells

Using a lentivirus vector, an expression vector containing human Oct3/4, Sox2, Klf4 and c-Myc was introduced into fibroblasts derived from the skin tissues of the abdominal portion of a healthy subject, so as to produce human induced pluripotent stem cells.

Specifically, a skin section was collected from a human abdominal portion, and it was then cultured in a culture solution (DMEM/10% bovine serum) in a cell culture plate. From 1 week after initiation of the culture, migration of fibroblasts from the skin section and the proliferation thereof were observed. Thus, using trypsin and EDTA, the fibroblasts were appropriately recovered and preserved in a frozen state.

The cDNAs of human Oct3/4, Sox2, Klf4 and c-Myc serving as reprogramming factors were each produced by the PCR method, using cDNA derived from human ES cells (KhES-1) or genomic DNA as a template. The thus produced cDNAs were each inserted into a plasmid vector (pENTR-D-TOPO; Gibco-Invitrogen). The nucleotide sequences of the cloned plasmid DNAs were confirmed by sequence analysis, and thereafter, using LR clonase (Gibco-Invitrogen), each DNA was introduced into a lentivirus vector (CSII-EF-RfA1; furnished from professor Miyoshi of RIKEN). In the case of Sox2 and c-Myc, LOX sequences were added to both termini of cDNA, after the DNA had been introduced into CSII-EF-RfA1.

Using a Cre structural gene as a template, a gene fragment was produced by the PCR method, and the produced gene fragment was then inserted into pCAGGS-IRES-Neo that was a vector driven by a CAG promoter, into which IRES (internal ribosomal entry site) and a neomycin resistance gene had been incorporated, so as to produce a vector that simultaneously expresses a Cre enzyme and a neomycin resistance gene.

Applying a lipofection method (Lipofectamine 2000, Invitrogen), each reprogramming factor which was introduced into CSII-EF which was produced above, a packaging construct, and envelope and Rev constructs were introduced into 293T cells. Three days after the gene introduction, the cell culture solution was recovered and was then passed through a 0.45-1 μm filter. Thereafter, viral particles were precipitated by a centrifugation method (50,000 G, 2 hours) and were then recovered. The recovered recombinant viral particles were suspended in a DMEM solution, and the obtained suspension was then dispensed into tubes for freeze preservation. The particles were preserved in a freezer (−80° C.) before use.

The cryopreserved human fibroblasts were thawed, and they were then cultured again for several days. Thereafter, a virus suspension was added to the cultured cells in a culture plate, so that the cells were infected with the virus, and thus, gene introduction was carried out. Four to six days after the gene introduction, the infected cells were recovered using trypsin-EDTA, and they were then subjected to co-culture with previously prepared mouse embryo-derived fibroblasts (feeder cells) whose proliferation had been terminated by treatment with mitomycin C. On the following day, the culture solution was replaced with a culture solution used for human ES cells, and the culture was then continued.

Twenty to thirty days after introduction of the reprogramming factor genes, using a microchip, colonies having an ES cell-like form were isolated as iPS cell clones from some cells under microscopic observation. The thus obtained cells were co-cultured with mouse embryo-derived feeder cells that had been prepared, separately. Thereafter, depending on the growth of the cells, the culture was continued while expanding the size of the culture vessel (the route shown in FIG. 4A). On the other hand, another portion of the cell population, into which the reprogramming factor genes had been introduced, was recovered using trypsin-EDTA, and introduction of a Cre expression vector was carried out (the route shown in FIG. 4B).

Introduction of Cre Expression Vector

Introduction of the Cre expression vector in the route shown in FIG. 4B was carried out by electroporation. For the purpose of selecting cells into which the Cre expression vector had been inserted, 24 to 48 hours after completion of the electroporation, G418 (Gibco-Invitrogen) was added to the culture solution, and the culture was then continued. Fifteen to Twenty-five days after completion of the electroporation, using a microchip, G418-resistant cell colonies having an ES cell-like form were isolated under microscopic observation. Thereafter, the cell colonies were subjected to co-culture with mouse embryo-derived feeder cells, which had been prepared, separately. Thereafter, depending on the growth of the cells, the culture was continued while expanding the size of the culture vessel.

The maintenance culture of human iPS cells was carried out in a human embryonic stem cell culture solution (DMEM-F12 (Wako Chemicals)/20% KSR (Gibco-Invitrogen)/bFGF (basic fibroblast growth factor: 10 ng/ml)/2-ME (2-mercaptoethanol, 50 μM)) on a culture dish made of polystyrene, using mitomycin C-treated mouse embryo fibroblasts as feeder cells.

Example 3

Introduction of Single-Chain Antibody Expression Vector into Human iPS Cells

The DNA of the single-chain antibody (scFv) expression vector (plasmid vector) produced in Example 1 was extracted from *Escherichia coli* according to an alkaline-SDS method, and it was then purified with an anion exchange column (Qiagen Plasmid Maxi kit; manufactured by Qiagen). The thus purified DNA was cleaved with a restriction enzyme PvuI to prepare linear DNA. Moreover, the linear DNA was purified using phenol and chloroform, and it was then recovered by isopropanol precipitation. Thereafter, the recovered DNA was washed with 70% ethanol, and it was then dissolved in a phosphate buffered saline (PBS).

The human iPS cells that had been subjected to the maintenance culture (the cell clones produced by the route shown in FIG. 4B) were recovered from the culture vessel using trypsin-EDTA (025% trypsin/1 mM EDTA), and they were then suspended in a DMEM solution ($1 \times 10^7$ cells/0.4 ml). The suspension was mixed with a plasmid vector (30 μg/0.1 ml) dissolved in PBS. Using a gene introduction device (Gene Pulser; manufactured by BioRad), gene introduction was carried out by electroporation (distance between electrodes of cuvette: 4 mm; energization: 200 V, 800 μF, once).

After completion of the electroporation, the culture was carried out for 24 hours in the presence of a Roh-binding kinase inhibitor (Y-27632; manufactured by Wako Pure Chemical Industries). Then, 48 hours after completion of the electroporation, puromycin (Sigma) was added to the culture solution, and the culture was then continued.

Thereafter, puromycin (5-15 μg/ml) was intermittently added to the culture solution, and the culture was further continued. Fifteen to eighteen days after completion of the electroporation, while observing the resultant culture under an inverted microscope, puromycin-resistant cell colonies were isolated using a microchip, and they were then subjected to co-culture with mouse embryo-derived feeder cells, which had been prepared, separately.

Subsequently, while expanding the size of the culture vessel depending on the growth of the cells, the culture was continued. Some portion was directly subjected to preservation in a frozen state. The other portion was induced to differentiate into macrophages, as described later.

Example 4

Induction of Differentiation of Human Induced Pluripotent Stem Cells into Macrophages (1) Preparation of OP9 Feeder Cells A mouse-derived culture cell line OP9 which was treated with mitomycin C (0.01 mg/ml, 60 minutes) was inoculated on a gelatin-coated dish, and it was then used from the following day forward.

(2) Differentiation Induction Culture

Undifferentiated iPS cells (those in the route A or B of FIG. 4) were treated with a CTK solution (collagenase-trypsin-KSR solution; Suemori et al., Biochemical and Biophysical Research Communications 345: 926-932, 2006) for 5 to 10 minutes. Thereafter, the cells were recovered with a culture solution containing FCS (fetal calf serum; manufactured by GIBCO-Invitrogen). The recovered cells were centrifuged, were then suspended in α-MEM/20% FCS, and were then inoculated on OP9 feeder cells. Thereafter, while exchanging the culture solution (α-MEM/20% FCS) with a fresh culture solution once three days, the culture was continued.

Fifteen to eighteen days after initiation of the differentiation induction, the cells were treated (37° C., 60 minutes) using a trypsin-EDTA-collagenase solution, so that they were dissociated and recovered. Then, a cell suspension was produced by pipetting. Thereafter, cells derived from a single dish were suspended in 10 ml of DMEM/10% FCS, and the obtained suspension was then dispersed on two 90-mm dishes, each of which contained no feeder cells and was not coated with gelatin. Two to five hours later, cells that had not adhered to the dishes were recovered, and the recovered cells were then passed through a 100-micron mesh (Cell Strainer; manufactured by BD Falcon), so as to obtain a cell population excluding cell masses. The thus obtained cells were suspended in α-MEM/20% FCS/human GM-CSF (100 ng/ml; manufactured by PeproTech)/human M-CSF (50 ng/ml; manufactured by PeproTech)/2-ME (0.05 mM), and the obtained suspension was inoculated again on OP9 feeder cells. Then, culture was carried out.

Seven to nine days after initiation of the culture, the cells were recovered by pipetting and were then suspended in RPMI-1640/10% FCS/M-CSF (100 ng/ml). The suspension was inoculated on a culture dish (manufactured by BD FALCON), and the culture was then carried out for 3 to 5 days, so as to produce macrophages (iPS-MP). FIG. 5 shows the images of iPS-MP in the dish, which were photographed using a phase-contrast microscopic lens. FIG. 5A shows the iPS-MP obtained by the route A of FIG. 4, namely, the iPS-MP derived from iPS cells into which a Cre expression vector and a scFv expression vector have not been introduced. FIG. 5B shows the iPS-MP obtained by the route B of FIG. 4, namely, the iPS-MP derived from iPS cells into which a Cre expression vector and a scFv expression vector have been introduced.

Example 5

Studies of Expression of Marker Molecules on Cell Surface of iPS-MP by Flow Cytometry The thus produced iPS-MP was recovered by pipetting. For the purpose of inhibiting non-specific binding of antibody, the iPS-MP was first treated with a Fc receptor blocking reagent (manufactured by Miltenyi Biotech) for 10 minutes.

Thereafter, using the following phycoerythrin (PE)-conjugated monoclonal antibody or fluorescein isothiocyanate (FITC)-conjugated monoclonal antibody, the iPS-MP was stained at room temperature for 40 minutes: PE-anti-human/mouse CD11b (clone M1/70, rat IgG2b), PE-anti-human CD14 (clone TUK4, mouse IgG2a), and FITC-anti-human CD68 (clone Y1/82A, mouse IgG2b). In addition, the iPS-MP was also stained with PE-rat IgG2b (clone LO-DNP-11), PE-mouse IgG2a (clone G155-178) and FITC-mouse IgG2b (clone 27-35) used as isotype-compatible control antibodies.

Thereafter, the cells were washed with PBS/2% FCS twice.

The washed cells were analyzed using a flow cytometric analysis apparatus (trade name: FACScan; manufactured by Becton Dickinson) equipped with CellQuest software.

FIG. 6 shows the results of the flow cytometric analysis conducted after antibody staining.

FIG. 6A shows the iPS-MP produced by the route shown in FIG. 4A, namely, the iPS-MP derived from iPS cells into which a Cre expression vector and a scFV expression vector have not been introduced. FIG. 6B shows the iPS-MP produced by the route shown in FIG. 4B, namely, the iPS-MP derived from iPS cells into which a Cre expression vector and a scFV expression vector have been introduced. Both types of iPS-MPs expressed CD11b, CD14 and CD68 on the cell surface, and they expressed the same marker molecules as those of physiologically existing human macrophages.

Example 6

Analysis of Binding Ability of iPS-MP Expressing Single-Chain Antibody Directed Against β-Amyloid Peptide, to Fluorescent Particles Coated with β-Amyloid Peptide in Suspending State (1) Coating of Fluorescent Particles with β-Amyloid Peptide To fluorescent particles (Sulfate Microspheres, Yellow-green, #F8828; manufactured by Molecular Probes), β-amyloid peptide (Amyloid β-Protein 1-42; Wako Chemicals) was added (final concentration: 0.03 mg/ml). While shaking at 25° C., the mixture was reacted for 12 hours. Thereafter, PBS containing 0.1% bovine serum albumin (PBS-BSA) was added thereto in an amount of two times the volume of the reaction solution. While shaking at 25° C., the mixture was further reacted for 2 hours. Fluorescent particles coated with only albumin were produced by reacting them in PBS-BSA for 14 hours, while shaking at 25° C.

Thereafter, the fluorescent particles were washed with PBS twice, and they were then stored in a refrigerator under light-shielded conditions before subjecting to experiments.

(2) Analysis of Binding Ability of iPS-MP to Fluorescent Particles iPS-MP, into which a single-chain antibody gene specific to β-amyloid had been introduced, was recovered from a culture dish, and it was then washed. Thereafter, the iPS-MP was mixed with β-amyloid-coated fluorescent particles (diameter: 0.2 μm) in a plastic test tube, and the obtained mixture was then left at rest at 37° C. for 90 minutes.

Thereafter, the reaction product was washed with PBS-FCS twice, and the fluorescence intensity of the iPS-MP, namely, the phagocytosis of the fluorescent beads was quantified using a flow cytometer.

FIG. 7 shows the results of the analysis by flow cytometry. By coating the fluorescent beads with β-amyloid, a larger number of cells bound to the beads (25.5→60.3%), and the number of the beads englobed by a single cell increased (mean fluorescence intensity: 781→1348).

Example 7

Analysis of Phagocytic Ability of iPS-MP Expressing Single-Chain Antibody Directed Against β-Amyloid Peptide, on β-Amyloid Peptide-Coated Fluorescent Particles in Adhesion Culture State (1) Coating of Fluorescent Particles with β-Amyloid Peptide To fluorescent particles (Sulfate Microspheres, Yellow-green, #F8828; manufactured by Molecular Probes), β-amyloid peptide (Amyloid β-Protein 1-42; Wako Chemicals) was added (final concentration: 0.03 mg/ml). While shaking at 25° C., the mixture was reacted for 24 hours. Thereafter, PBS containing 2% bovine serum albumin (PBS-BSA) was added in an equal amount to the reaction solution. While shaking at 25° C., the mixture was further reacted for 24 hours. Fluorescent particles coated with only albumin, which were to be used in a control experiment, were produced by reacting them in PBS-BSA for 48 hours, while shaking at 25° C.

Thereafter, the fluorescent particles were washed with PBS twice, and they were then stored in a refrigerator under light-shielded conditions before subjecting to experiments.

(2) Analysis of Phagocytic Ability of iPS-MP on Fluorescent Particles iPS-MP, into which a single-chain antibody gene specific to β-amyloid had been introduced, was inoculated on a cell culture vessel (a 24-well culture plate). After the cells had adhered to the culture plate, fluorescent beads (diameter: 0.2 μm), which were coated or were not coated with β-amyloid, were added thereto. The obtained mixture was then cultured at 37° C. for 16 hours.

As shown in FIG. 8, it was confirmed using a phase-contrast lens that the iPS-MP performed phagocytosis on the fluorescent beads. The left photograph in FIG. 8 is a bright-field image photographed using a phase-contrast lens, and it shows the form of the iPS-MP. The right photograph in FIG. 8 is a fluorographic image. It shows location of the fluorescent beads, and also shows that the fluorescent beads were incorporated into the iPS-MP cells.

The iPS-MP was recovered from the culture plate, and the amount of beads englobed by the iPS-MP was then quantified using a flow cytometer. First, all of the iPS-MP existing in the wells of the culture plate was recovered. Subsequently, for the purpose of recovering cells that strongly adhered to the wells, a 0.25% trypsin/1 mM EDTA solution was added to the culture plate, and it was then incubated for 30 minutes. Thereafter, the cells were recovered using a pipette. Subsequently, using a flow cytometer, the fluorescence intensity of the iPS-MP, namely, the amount of the fluorescent beads englobed by a single iPS-MP cell was quantified.

FIG. 9 shows the results of the analysis using the flow cytometer. The left panel shows the analysis results of iPS-MP, to which β-amyloid-not-coated beads had been added. The right panel shows the analysis results of iPS-MP, to which β-amyloid-coated beads had been added. The iPS-MP had higher fluorescence intensity, namely, a single iPS-MP cell englobed a larger number of beads, in a case in which the β-amyloid-coated beads had been added, than in a case in which the β-amyloid-not-coated beads had been added. These results showed that iPS-MP expressing a single-chain antibody specific to β-amyloid performs phagocytosis more efficiently on β-amyloid-coated beads, than on β-amyloid-not-coated beads.

FIG. 10 is a graph that was made based on the mean values of fluorescence intensity of iPS-MP in a case in which the concentrations of beads added to the iPS-MP were changed. The open circle indicates a case in which β-amyloid-not-coated beads were added. The filled circle indicates a case in which β-amyloid-coated beads were added. The horizontal axis of the graph indicates the concentration of beads added to iPS-MP, and the longitudinal axis thereof indicates the fluorescence intensity of the recovered cells. The results shown in this figure demonstrated that the amount of beads englobed by iPS-MP change depending on the concentration of the added beads. In all of the relative concentrations of the beads that were 10 or greater, as shown in the graph, the iPS-MP expressing a single-chain antibody specific to β-amyloid performed phagocytosis more efficiently on β-amyloid-coated beads, than on β-amyloid-not-coated beads.

Example 8

The in vitro effect of iPS-MP expressing a single-chain antibody directed against human CD20 molecules on a human B lymphoblastic leukemia cell line BALL-1 expressing the CD20 molecules was analyzed. The iPS-MP ($2.5 \times 10^4$ cells/well) wherein a CD20-specific single-chain antibody gene was introduced or the iPS-MP ($2.5 \times 10^4$ cells/well) wherein a CD20-specific single-chain antibody gene was not introduced, were inoculated into a cell culture vessel (a 96-well flat-bottom culture plate). On the following day, BALL-1 cells ($2.5 \times 10^3$ cells/well), in which a fire fly-derived luciferase as a photoprotein had been expressed by gene introduction, was added to the culture vessel, and they were then cultured. As a culture solution, RPMI-1640 medium/10% bovine serum/M-CSF (50 ng/ml)/GM-CSF (100 ng/ml)/interferon gamma (500 units/ml) was used.

The culture was further carried out for 3 days, and each well was fully stirred by a pipetting operation. Thereafter, 0.1 ml of the culture solution containing suspending cells was recovered into a plate for luminescence measurement (B&W Isoplate; Wallac). Thereafter, a luciferase substrate solution (Steadyliteplus; PerkinElmer) was added thereto, and luciferase activity, namely, the number of BALL-1 cells contained in the sample was measured using a luminometer (Tristar LB941, Berthold Technologies).

FIG. 11 shows the experimental results. When iPS-MP expressing a single-chain antibody specific to CD20 was added and cultured, luciferase activity was 1/100 or less of the case of culturing only BALL-1 cells, or the case of adding iPS-MP that did not express a single-chain antibody and then culturing it. These results showed that the iPS-MP expressing a single-chain antibody specific to CD20 has the effect of suppressing the growth of BALL-1 cells or killing such BALL-1 cells in a culture vessel.

Example 9

The in vivo effect of iPS-MP expressing a single-chain antibody directed against human CD20 molecules on a human B lymphoblastic leukemia cell line BALL-1 expressing the CD20 molecules was analyzed. BALL-1 cells ($5 \times 10^6$ cells/mouse) expressing luciferase and interferon gamma (20,000 units/mouse) were injected into the abdominal cavity of severe combined immunodeficiency mice (scid mice) that lacked T lymphocytes and B lymphocytes. Moreover, in addition to this injection, iPS-MP ($2 \times 10^7$ cells/mouse) that did not express a single-chain antibody was injected into a group of mice. Furthermore, in addition to these injections, iPS-MP ($2 \times 10^7$ cells/mouse) expressing a single-chain antibody specific to CD20 was injected into another group of mice. Three days later, the mice were sacrificed, and omental tissues were excised from the mice. Thereafter, luciferase activity in an extract of the omental tissues was measured, so as to measure the number of BALL-1 cells existing in the omental tissues.

FIG. 12 shows the experimental results. In the group in which iPS-MP expressing a single-chain antibody specific to CD20 was added and cultured, luciferase activity of the omental tissues was 1/100 or less, when compared with the group in which only BALL-1 cells were injected, or the group in which iPS-MP that did not express a single-chain antibody was added in addition to BALL-1 cells and cultured. These results showed that the iPS-MP expressing a single-chain antibody specific to CD20 has the effect of suppressing the growth of BALL-1 cells or killing such BALL-1 cells in the abdominal cavity tissue of immunodeficiency mice.

The invention claimed is:

1. A method of making a macrophage that expresses an antibody directed against a β-amyloid protein comprising:
   introducing a vector encoding an antibody directed against a β-amyloid protein into an induced pluripotent stem (iPS) cell, wherein the antibody directed against a β-amyloid protein comprises the amino acid sequence of SEQ ID NO:8 and the amino acid sequence of SEQ ID NO:10; and
   differentiating the iPS cell into a macrophage, such that the macrophage expresses the antibody directed against a β-amyloid protein.

2. The method according to claim 1, wherein the vector is a plasmid vector.

3. The method according to claim 1, wherein the vector comprises a drug resistance gene.

4. The method according to claim 1, wherein differentiating the iPS cell comprises culturing a cell derived from the iPS cell in the presence of a granulocyte-macrophage colony-stimulating factor (GM-CSF) and/or a macrophage colony-stimulating factor (M-CSF).

5. The method according to claim 1, wherein differentiating the iPS cell comprises:
   (A) allowing the iPS cell, into which the vector has been introduced, to differentiate into a cell group containing mesodermal cells; and
   (B) co-culturing the cell group containing mesodermal cells in the presence of a granulocyte-macrophage colony-stimulating factor (GM-CSF), so as to obtain a cell group containing macrophages having phagocytic ability.

* * * * *